United States Patent [19]

Si-Hoe et al.

[11] Patent Number: 5,054,149
[45] Date of Patent: Oct. 8, 1991

[54] ELECTRIC TOOTHBRUSH

[76] Inventors: Kok S. Si-Hoe, No. 16, Greenview Crescent, Singapore 1128; Tiong E. Ong, Block 10-D, Braddell View Estate No. 20-13, Singapore, both of Singapore

[21] Appl. No.: 378,806

[22] Filed: Jul. 12, 1989

[30] Foreign Application Priority Data

Jul. 14, 1988 [GB] United Kingdom ............... 8816775

[51] Int. Cl.$^5$ .............................................. A46B 13/02
[52] U.S. Cl. ......................................... 15/28; 15/22.1; 433/131; 74/70; 74/25
[58] Field of Search ................... 15/28, 22 R, 23, 24, 15/29; 128/49, 62 A, 62 R; 74/70, 25; 433/131, 114, 118

[56] References Cited

U.S. PATENT DOCUMENTS

| | | | |
|---|---|---|---|
| 3,939,599 | 2/1976 | Henry et al. | 15/28 |
| 4,432,729 | 2/1984 | Fattaleh | 15/22 R |
| 4,827,550 | 5/1989 | Graham et al. | 15/28 |
| 4,827,552 | 5/1989 | Bojor et al. | 15/28 |

FOREIGN PATENT DOCUMENTS 3233266 10/1983 Fed. Rep. of Germany ...... 433/118

Primary Examiner—Philip R. Coe
Assistant Examiner—Gary K. Graham
Attorney, Agent, or Firm—Cushman, Darby & Cushman

[57] ABSTRACT

An electric toothbrush comprises two main casings, a battery/motor casing and a brush drive casing, both casings being made of plastics material and one casing telescopically fitting over the other. The casing contains a battery, a motor and a motor shaft which carries the first gear of a reduction gear set which also comprises gears which drive a motor gear output shaft carrying a male coupling. The brush drive casing carries a brush head further reduction gearing and a brush drive shaft which carries a female coupling. When the couplings are mated telescopically, the male and female couplings connect so as to complete the drive to the toothbrush head. Preferably the toothbrush head is arranged to be driven in alternate directions, i.e., so as to have a reciprocal motion.

2 Claims, 4 Drawing Sheets

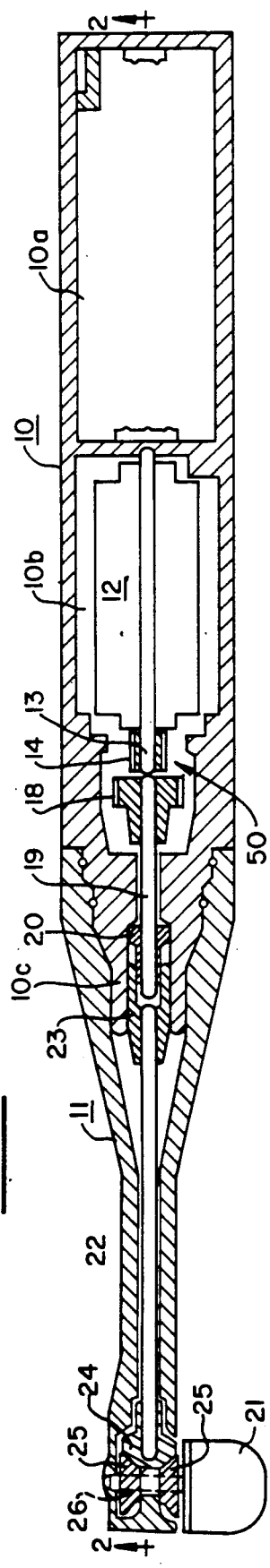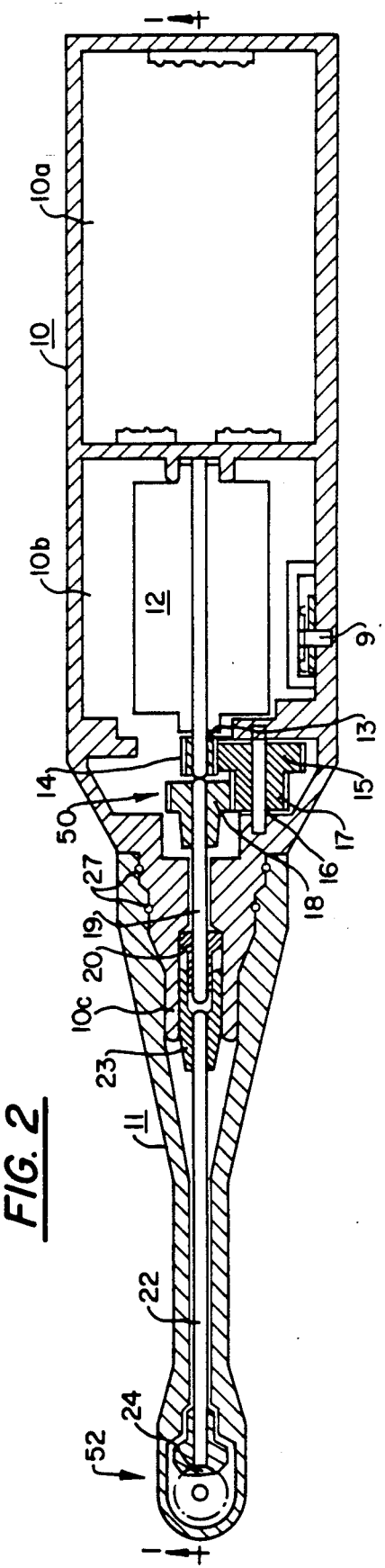

ELECTRIC TOOTHBRUSH

BACKGROUND OF THE INVENTION

This invention relates to an electric toothbrush the type in which a motor, driven by batteries, is contained in a casing and, through gearing and drive shafts, drives a rotary toothbrush head.

The invention is related to and is, in some ways, an improvement upon the toothbrush described in our copending UK patent application 8726754 now UK patent 2212570.

SUMMARY OF THE INVENTION

An object of the present invention is to provide a rotary or reciprocatory rotary toothbrush in compact form.

According to one aspect of the present invention an electric toothbrush comprises a battery/motor compartment which contains gearing driven by the motor and one part of a two-part coupling, and a brush holder casing which includes a brush drive shaft, and optionally gearing, and the second part of the two part coupling, the two casings being so arranged that one caswing may be telescoped over the other so as to engage the coupling to enable the drive from the motor via the gearing to drive a brush head.

Preferably the motor/battery casing contains reduction gearing.

The head may be driven in such a way as to produce an alternately reciprocating motion or reversing motion so that the head rotates through a small arc in one direction and then through a similar arc in the opposite direction in rapid succession.

This may be achieved by use of gearing in which a quadrant gear has a proportion of its gear teeth omitted so that the quadrant gear alternately drives two bevel gears, one gear being driven in one direction and the other gear in the other direction so as to produce the desired motion.

BRIEF DESCRIPTION OF THE DRAWINGS

In the accompanying drawings: FIG. 1 is a vertical longitudinal sectional view of a first embodiment of an electric toothbrush embodying the invention, this section being taken on line 1—1 of FIG. 2;

FIG. 2 is a horizontal longitudinal section view on line 2—2 shown in FIG. 1, of the same toothbrush;

DETAILED DESCRIPTION

Figure 4:
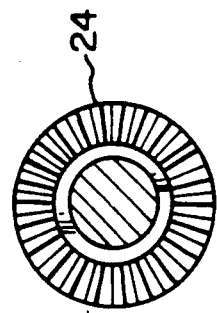
FIGS. 3 and 4 illustrate exemplary forms of the gearing arrangements for the embodiment shown in FIGS. 1 and 2.

In FIG. 1 the electric toothbrush comprises two main parts, a battery/motor casing 10 made of plastics material and a brush drive casing 11, also made of plastics material which is telescopically fitted over and sealed to the casing 10.

The casing 10 has compartments 10a for the battery and 10b for the motor and reduction gearing. The motor 12 drives a motor shaft 13 which carries the first gear 14 of a reduction gear set 50 producing a gear ratio of 1:4.5 so as to reduce the 6,500 RPM output of a motor to a more suitable output for driving a toothbrush.

The gear set 50 which, in other words, is a first mechanical power transmitting means 50 comprises the gear 14 and a pair of gears 15 and 17 mounted on a shaft 16. Gear 17, in turn, drives a gear 18 to drive a motor gear output shaft 19 carrying at one end a male couple 20, in other words, a first mechanical power transmitting coupling element 20. Motor 12 is operated by switch 9 and the batteries in the battery compartment 10a may be in the form of two cells, such as U2 cells.

The battery motor casing with its battery, motor, reduction gearing, and output shaft driving male coupling form one complete integral unit.

A second unit consists of brush drive casing 11 carrying a brush head 21, further reduction gearing 52, which, in other words, is a second mechanical power transmitting means 52 (including gears 24 and 25) and a brush drive shaft 22. At one end of the brush drive shaft is a femal coupling 23, in other words, a second mechanical power transmitting element 23 adapted to mate with the male coupling 20 so as to convey the drive via brush drive shaft 22 to a quadrant gear 24 in turn arranged to drive a set of bevel gears 25 on a shaft 26 which carries the brush head 21. The shaft 26, in other words, is a holder for the brush head 21.

The brush drive casing 11 is push-fit onto the end 10c of the motor casing 10 and there are seals 27 between the motor casing 10 and the brush casing 11.

The brush drive casing 11 together with its brush head, bevel gearing and brush drive shaft which carries the female coupling, are an integral unitary structure which may be removed and replaced on the casing 10, for example to change brush heads or to clean various parts of the toothbrush.

The gearing 52 in the brush head may be a straightforward drive gearing or it may be of the type described and claimed in the specification of our copending UK patent application No. 8726754. In that specification, there is described a form of gearing (also illustrated in FIG.S 3 and 4 hereof) in which a crown gear drives two bevel gears and the crown gear has teeth missing over a predetermined limited arc. The teeth may extend through as little as 45°-60° around the gear face so that as the crown gear is rotated it alternately drives one and then the other bevel gear to produce an alternately reversing rotary action of the brush head.

Figure 5:
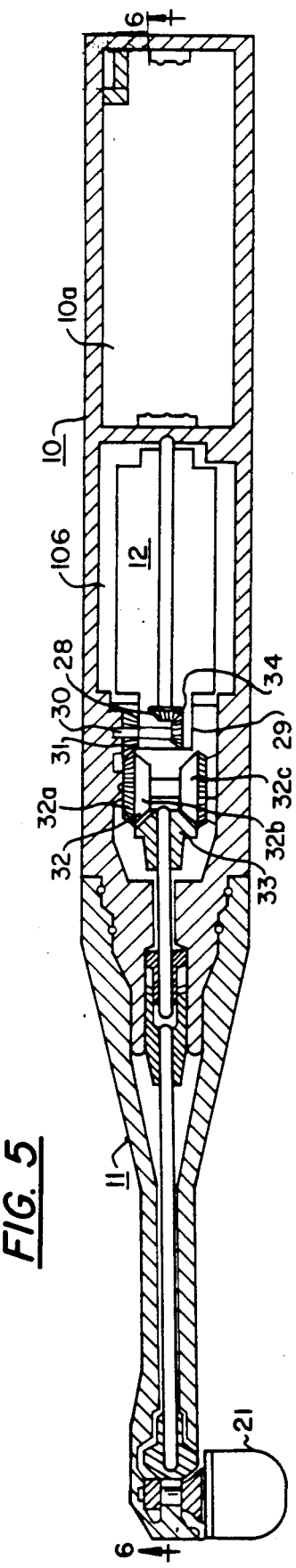
FIG. 5 is a vertical longitudinal sectional view of another embodiment of the invention, the elevation being taken on line 5—5 shown in FIG. 6.
Figure 6:
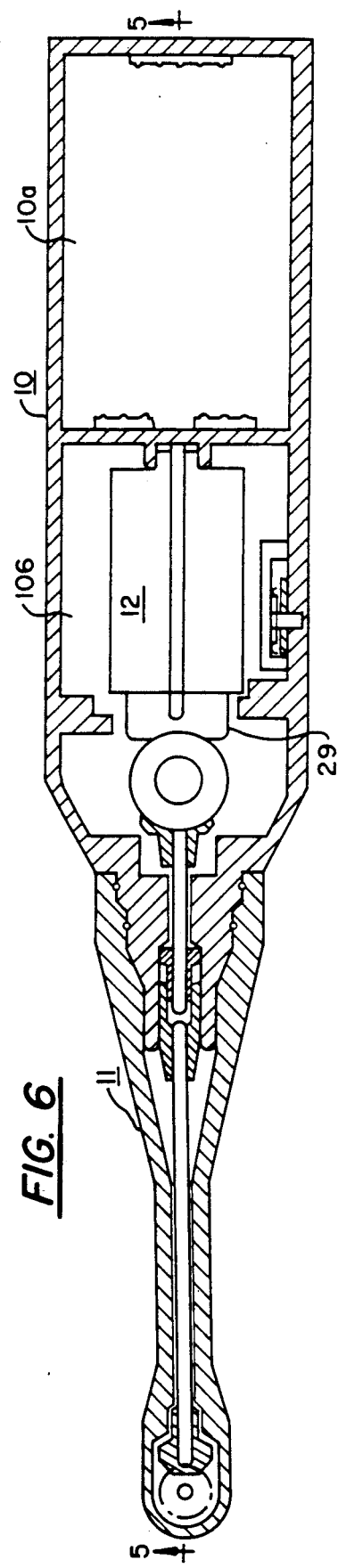
FIG. 6 is a horizontal longitudinal sectional view taken on line 6—6 of FIG. 5, of the same embodiment of the invention.
Figure 8:
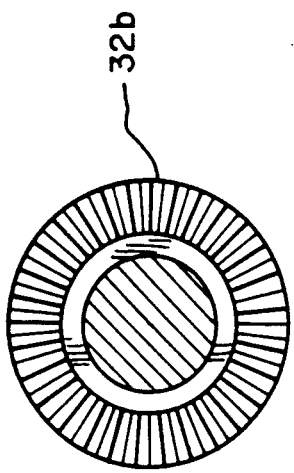
FIGS. 7-9 illustrate exemplary forms of the gearing arrangements for the embodiment shown in FIGS. 5 and 6.
Figure 7:
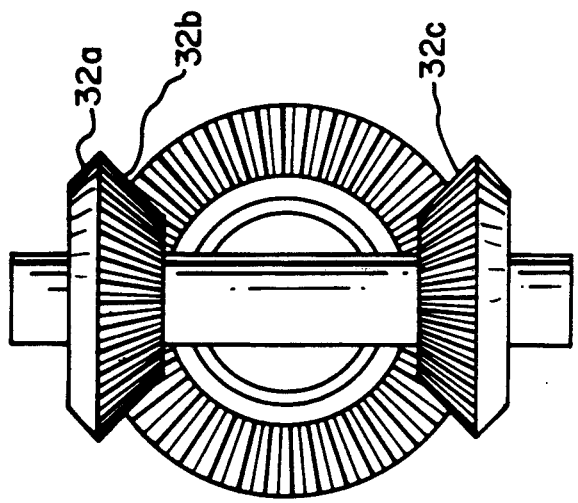
Figure 3:
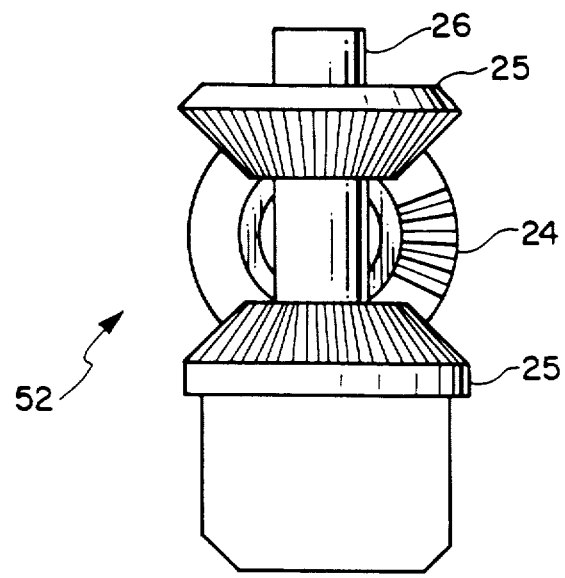
Figure 4:
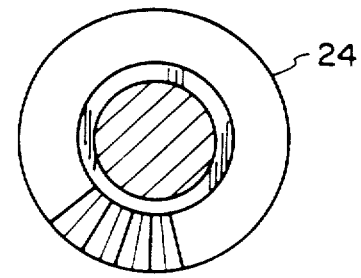
Figure 7:
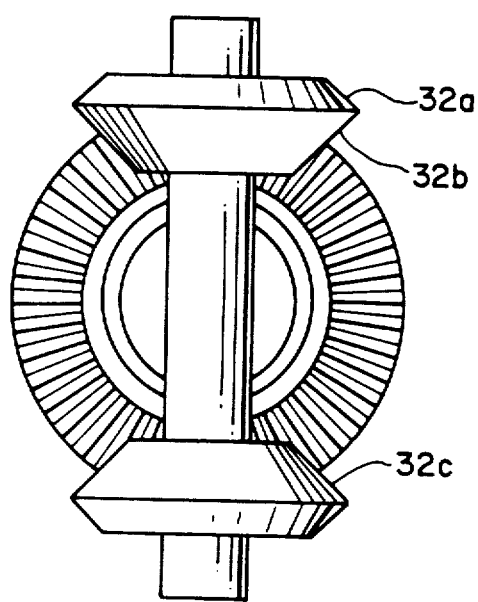
Figure 8:
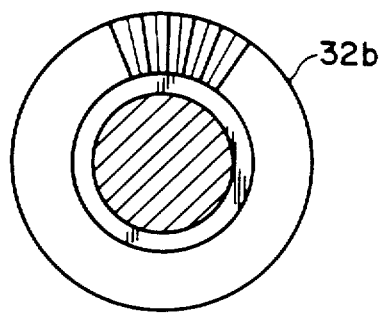
Figure 9:
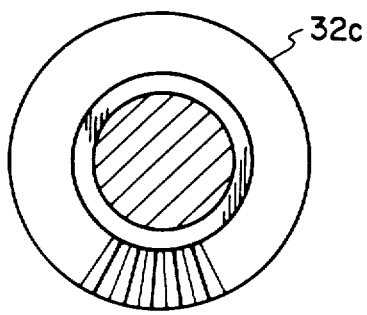

In the second embodiment of the present invention shown in FIGS. 5-8 there are again two casings, a battery/motor casing 10 and a brush drive casing 11 which are connected and sealed together in the same way as described with reference to FIGS. 1 and 2.

Again there is a battery compartment 10a and a motor compartment 10b containing a motor 12.

The brush head 21 and the components generally within the brush drive casing 11 are the same as described with reference to FIGS. 1 and 2. There is a similar coupling.

The difference in this embodiment as compared with the first embodiment lies in the way in which the drive is transmitted from the motor 12 to the coupling.

Figure 3:
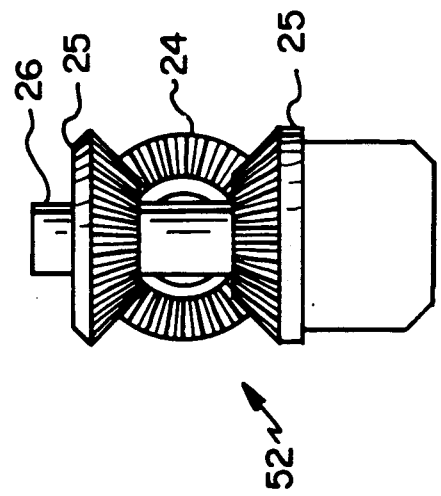
Figure 9:
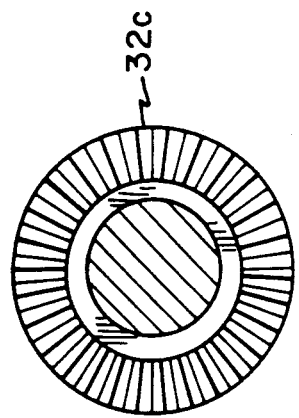

The motor 12 has a motor drive shaft 28 which through bevel gears 34 contained in a gearbox 29 drives a shaft 30. Attached to shaft 30 is a bevel gear 31 driving a special gear 32 which is in two parts. The upper part, as seen in FIGS. 3-9; 32a is a straightforward bevel gear. The lower part 32b is a bevel gear with a number of teeth removed. Similarly bevel gear 32c has a number of teeth removed. The gears 32b and 32c together drive crown wheel 33 but because of the teeth which are removed on the two gears the crown wheel will be driven alternatively in one direction and then in the other so that the drive transmitted to the brush head is an alternately reversing motion.

This gearing is just one of several ways by which a purely rotary motion may be converted to an alternately clockwise and anti-clockwise rotational motion. It may also be dome by link mechanisms and other well known mechanisms. It is used in this document as an illustration of the way in which the brush head 21 is driven via the quick coupling and pair of bevel gears, which operate in the way described with reference to FIGS. 1-4.

I claim:

1. An electric toothbrush, comprising:
   a first member including: an electric motor having a rotary output shaft, a longitudinally elongated housing containing said motor and including a compartment for electric power storage battery means for powering said motor and a forward end of said housing configured for removable connection with a second member, a first mechanical power transmitting coupling element which is accessible at said end of said housing of said first member, and first mechanical power transmitting means operatively connecting said rotary output shaft with said first mechanical power transmitting coupling element; and
   a second member including: a longitudinally elongated casing, a holder for a brush head, said holder being mounted to said casing for reversing rotation about an axis generally transverse to the longitudinal axis of said casing adjacent an outer end of said casing, a drive shaft journalled in said casing for rotation about the longitudinal axis thereof, said casing having a rear end configured for removable connection with said forward end of said first member, a second mechanical power transmitting means operatively connecting said holder with said drive shaft, and said drive shaft having a second mechanical power transmitting coupling element which is accessible at said rear end of said casing of said second member;
   said forward end of said housing of said first member being removably connected with said rear end of said casing of said second member, and said first mechanical power transmitting coupling element being telescopically operatively removably coupled with said second mechanical power transmitting coupling element;
   one of said first and second mechanical power transmitting means being arranged for converting a continuous unidirectional rotary input from the respective of said rotary output shaft and said drive shaft, into a periodically reversing rotary output about an axis of oscillation to the respective of said first mechanical power transmitting coupling element and said holder; said one of said first and second mechanical power transmitting means being characterized by not reciprocating longitudinally of said axis of oscillation while rotating about said axis of oscillation;
   said second mechanical power transmitting means comprising a quadrant gear mounted for alternate driving relation with two bevel gears arranged for being driven in rotationally opposite directions to one another by said quadrant gear about said axis of oscillation.

2. An electric toothbrush, comprising:
   a first member including: an electric motor having a rotary output shaft, a longitudinally elongated housing containing said motor and including a compartment for electric power storage battery means for powering said motor and a forward end of said housing configured for removable connection with a second member, a first mechanical power transmitting coupling element which is accessible at said end of said housing of said first member, and first mechanical power transmitting means operatively connecting said rotary output shaft with said first mechanical power transmitting coupling element; and
   a second member including: a longitudinally elongated casing, a holder for a brush head, said holder being mounted to said casing for reversing rotation about an axis generally transverse to the longitudinal axis of said casing adjacent an outer end of said casing, a drive shaft journalled in said casing for rotation about the longitudinal axis thereof, said casing having a rear end configured for removable connection with said forward end of said first member, a second mechanical power transmitting means operatively connecting said holder with said drive shaft, and said drive shaft having a second mechanical power transmitting coupling element which is accessible at said rear end of said casing of said second member;
   said forward end of said housing of said first member being removably connected with said rear end of said casing of said second member, and said first mechanical power transmitting coupling element being telescopically operatively removably coupled with said second mechanical power transmitting coupling element;
   one of said first and second mechanical power transmitting means being arranged for converting a continuous unidirectional rotary input from the respective of said rotary output shaft and said drive shaft, into a periodically reversing rotary output about an axis of oscillation to the respective of said first mechanical power transmitting coupling element and said holder; said one of said first and second mechanical power transmitting means being characterized by not reciprocating longitudinally of said axis of oscillation while rotating about said axis of oscillation;
   said first mechanical power transmitting means comprising two bevel gears each lacking teeth throughout an arc of predetermined angular extent and mounted for alternate driving relation with a crown gear wheel arranged for being driven in rotationally opposite directions alternately by respective ones of said bevel gears about said axis of oscillation.

* * * * *

UNITED STATES PATENT AND TRADEMARK OFFICE
CERTIFICATE OF CORRECTION

PATENT NO. : 5,054,149

DATED : October 8, 1991

INVENTOR(S) : Kok Soon Si-Hoe and Tiong Ee Ong

It is certified that error appears in the above-identified patent and that said Letters Patent is hereby corrected as shown below:

Please correct Figures 3, 4, 7, 8 and 9 as shown on the attached sheets.

Signed and Sealed this

Sixth Day of April, 1993

*Attest:*

STEPHEN G. KUNIN

*Attesting Officer*  *Acting Commissioner of Patents and Trademarks*